United States Patent
Chang

(10) Patent No.: US 6,705,322 B2
(45) Date of Patent: Mar. 16, 2004

(54) LARYNGEAL MASK AIRWAY

(76) Inventor: Ti-Li Chang, 9F-7, No. 1, Lane 641, Shen-Lin S. Rd., Ta Ya Hsiang, Taichung Hsien (TW)

(*) Notice: Subject to any disclaimer, the term of this patent is extended or adjusted under 35 U.S.C. 154(b) by 0 days.

(21) Appl. No.: 10/120,438

(22) Filed: Apr. 12, 2002

(65) Prior Publication Data

US 2003/0192548 A1 Oct. 16, 2003

(51) Int. Cl.[7] .............................................. A61M 16/00
(52) U.S. Cl. ............................. 128/207.15; 128/207.14
(58) Field of Search ........................ 128/207.14, 207.15, 128/207.16, 206.26, 200.26, 200.24, 205.24, 207.12; 604/96.01, 101.02, 102.01

(56) References Cited

U.S. PATENT DOCUMENTS

| 4,509,514 A | * | 4/1985 | Brain | 128/207.15 |
|---|---|---|---|---|
| 5,632,271 A | * | 5/1997 | Brain | 128/207.15 |
| 5,638,812 A | * | 6/1997 | Turner | 128/207.14 |
| 5,682,880 A | * | 11/1997 | Brain | 128/207.15 |
| 5,743,258 A | * | 4/1998 | Sato et al. | 128/207.15 |
| 6,012,452 A | * | 1/2000 | Pagan | 128/200.26 |
| 6,095,144 A | * | 8/2000 | Pagan | 128/207.15 |
| 6,152,136 A | * | 11/2000 | Pagan | 128/207.15 |
| 6,240,922 B1 | * | 6/2001 | Pagan | 128/207.15 |
| 6,318,367 B1 | * | 11/2001 | Mongeon | 128/207.15 |
| 6,394,093 B1 | * | 5/2002 | Lethi | 128/207.18 |
| 2001/0025641 A1 | * | 10/2001 | Doane et al. | 128/207.15 |
| 2002/0078961 A1 | * | 6/2002 | Collins | 128/207.15 |

* cited by examiner

Primary Examiner—Aaron J. Lewis
Assistant Examiner—Teena Mitchell
(74) Attorney, Agent, or Firm—Rosenberg, Klein & Lee

(57) ABSTRACT

A laryngeal mask tube consists of a dual-airway tube (10), a mask (20) with an inflatable bladder (24) and an inflation indicator device (30). The dual-airway tube (10) comprises a simplified primary tube (12) and secondary tube (14) integrally combined together. The primary tube (12) communicates with the mask (20) to guide gas into the body of a patient and the secondary tube (14) communicates between with the bladder (24) and the inflation indicator device (30) to monitor and inflate the bladder (24). Moreover, two ribs (26) are formed in the mask to prevent blockage of the primary tube (12) and a tongue (242) is formed inside the bladder (24) to prevent the bladder (24) from folding and preventing a seal around the larynx. Whereby, the laryngeal mask airway is convenient and efficient to use.

8 Claims, 6 Drawing Sheets

LARYNGEAL MASK AIRWAY

BACKGROUND OF THE INVENTION

1. Field of the Invention

The present invention relates to a laryngeal mask airway for use with patients who are not able to breathe, and more particularly to a laryngeal mask airway that is efficient and convenient to use.

2. Description of Related Art

With reference to FIGS. 5 and 6, a conventional laryngeal mask airway in accordance with the prior art comprises an airway tube (60), a laryngeal mask (70) and a laryngeal mask inflation tube (74).

The airway tube (60) is a large-bore tube made of resilient plastic material and has one end connected to the laryngeal mask (70). The laryngeal mask (70) is teardrop-shaped and divided into a curved bottom face (not numbered) and a bladder (72) around the curved bottom face. Multiple ventilation holes (71) are defined in the curved bottom face to connect the laryngeal mask (70) to the airway tube (60). The bladder (72) is inflatable and has a distal pointed end (not numbered) and a rear obtuse end (not numbered). The laryngeal mask inflation tube (74) has two ends (not numbered). One end connects to the rear obtuse end of the bladder (72). The other end of the laryngeal inflation tube (74) is a free end. An inflation indictor balloon (76) with a valve (77) is attached to the free end.

When the laryngeal mask airway is used to allow a patient to breathe, the laryngeal mask (70) is carefully flattened against the esophagus and the the pointed end of the bladder (72) is pushed into the esophagus until the ventilation holes (71) communicate with the larynx of the patient. With the bladder (72) around the opening to the larynx, a syringe (not shown) connects to the valve (77) to inject air into the bladder (72) via the laryngeal mask inflation line (74) to make the bladder (72) inflate. Thereby, no gap is formed between the bladder (72) and the larynx, and anesthetic gas can be injected into the lungs of the patient without any gas leakage. Meanwhile, the inflation indicator balloon (76) reflects the degree to which the bladder (72) is inflated so that medical personnel can observe and adjust the inflation of the bladder (72) as necessary.

However, the laryngeal mask airway still has the following drawbacks.

1. The bladder (72) usually has a pressure of 60–120 cm H2O when the bladder (72) is inflated with 20–30 cc of air. Under this pressure, the mucous membrane of the larynx is easily damaged thereby causing ulceration of the larynx. If the pressure is reduced, the bladder (72) does not seal the larynx well, and the anesthetic gas easily escapes through the gaps.

2. The bladder (72) easily refolds at the pointed end when pressed against the esophagus. The refolded portion of the bladder (72) makes the patient uncomfortable, can cause the patient to reflexively vomit, which displaces the laryngeal mask airway from the necessary position guide the anesthetic gas to the lungs, thereby allowing the gas to escape.

3. The ventilation holes (71) in the mask (70) are covered completely or partially by epiglottis. Thus the anesthetic gas cannot flow freely into the lungs.

4. The airway tube (60) and the laryngeal mask inflation tube (74) are separate so that the laryngeal mask inflation tube (74) has to be carefully manipulated when the laryngeal mask airway insert into the esophagus of the patient and can cause troublesome operational problems.

The present invention has arisen to mitigate and/or obviate the disadvantages of the conventional laryngeal mask airway.

SUMMARY OF THE INVENTION

The main objective of the present invention is to provide an improved laryngeal mask airway that is easily operated and efficiently conducts anesthetic gas into the larynx and ultimately the lungs of a patient.

Further benefits and advantages of the present invention will become apparent after a careful reading of the detailed description with appropriate reference to the accompanying drawings.

DETAILED DESCRIPTION OF THE INVENTION

Figure 1:
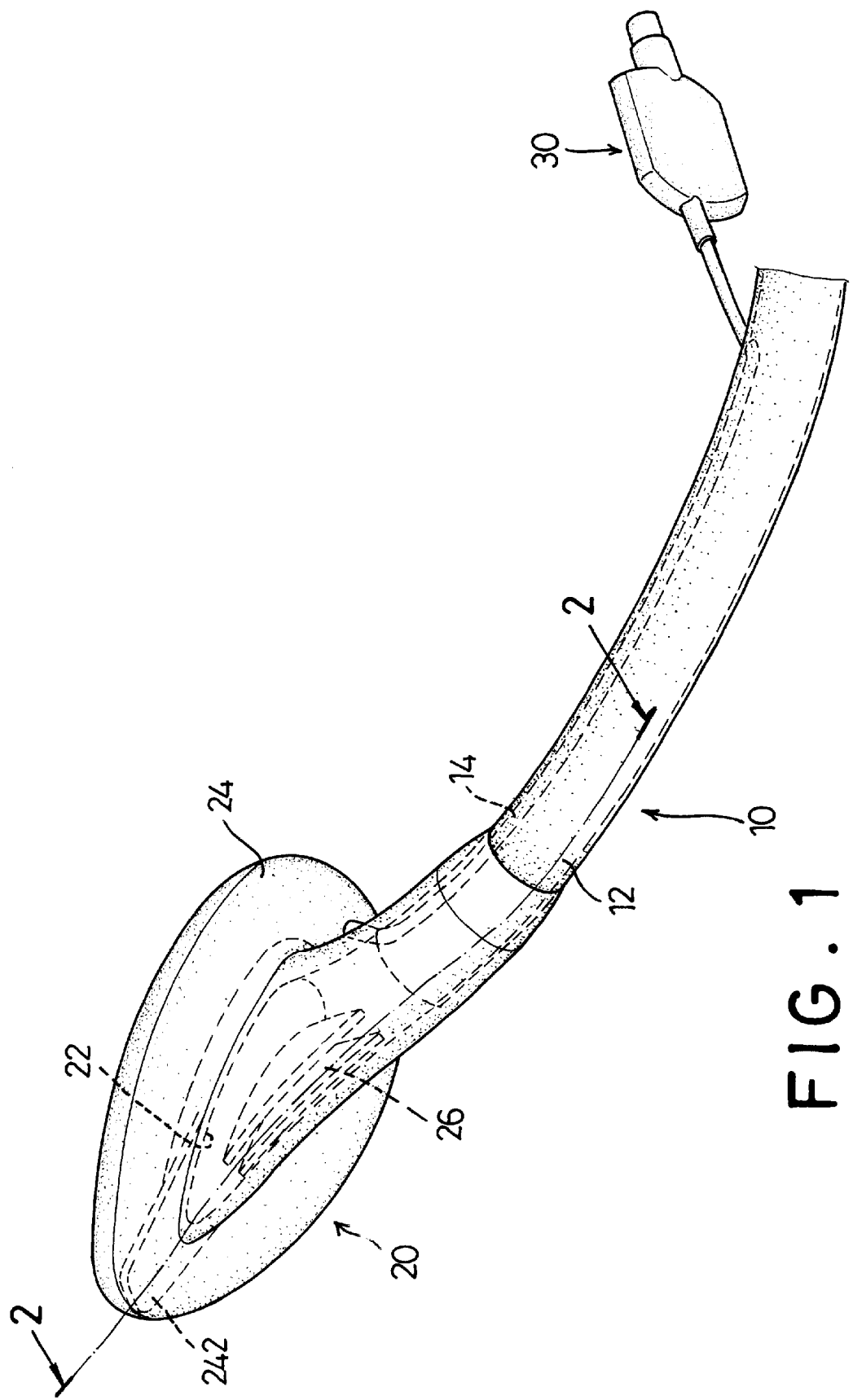
FIG. 1 is a perspective view of a laryngeal mask airway in accordance with the present invention.
Figure 2:
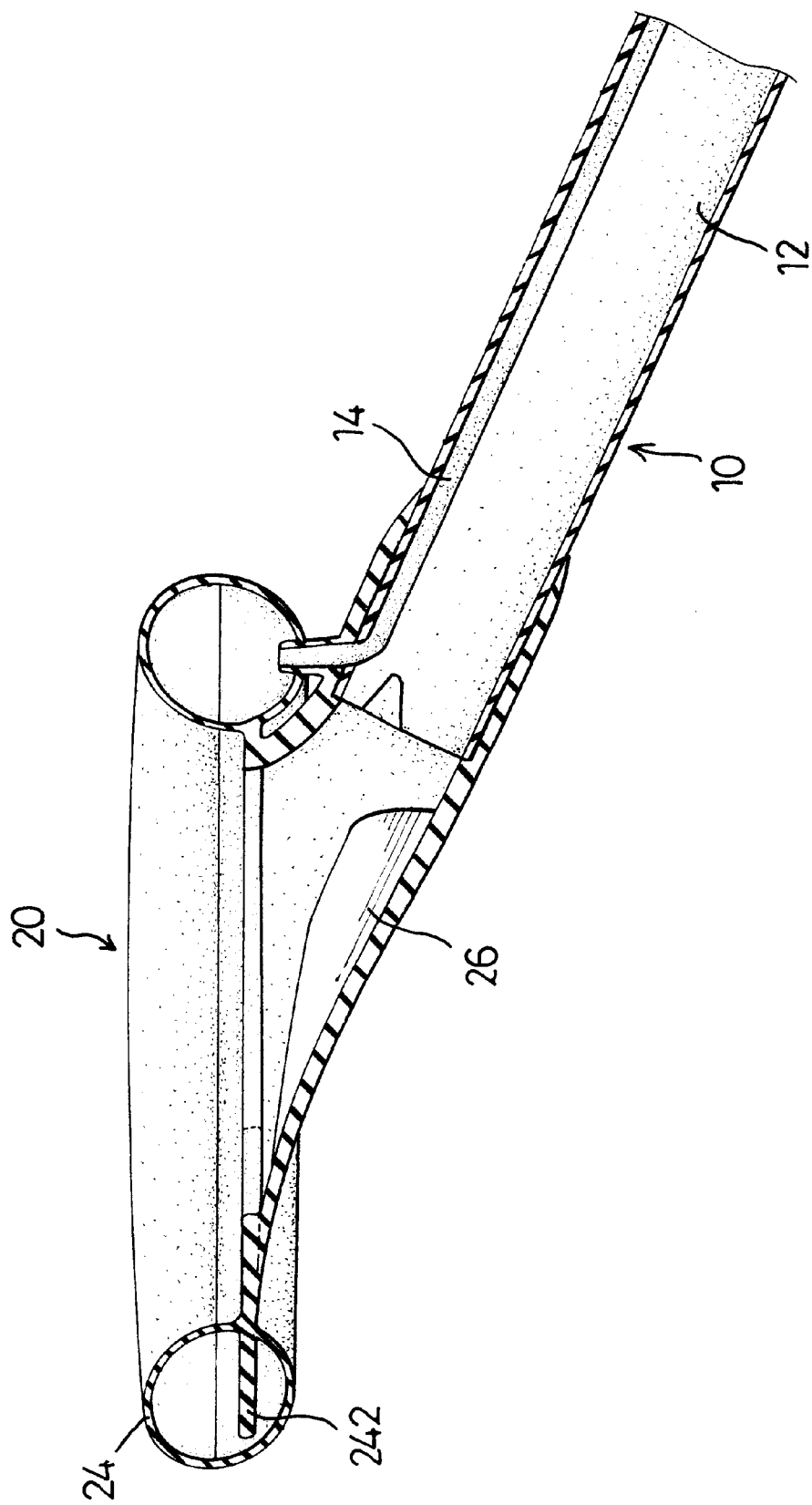
FIG. 2 is a cross-sectional side plan view of the laryngeal mask airway along line 2—2 in FIG. 1.
Figure 3:
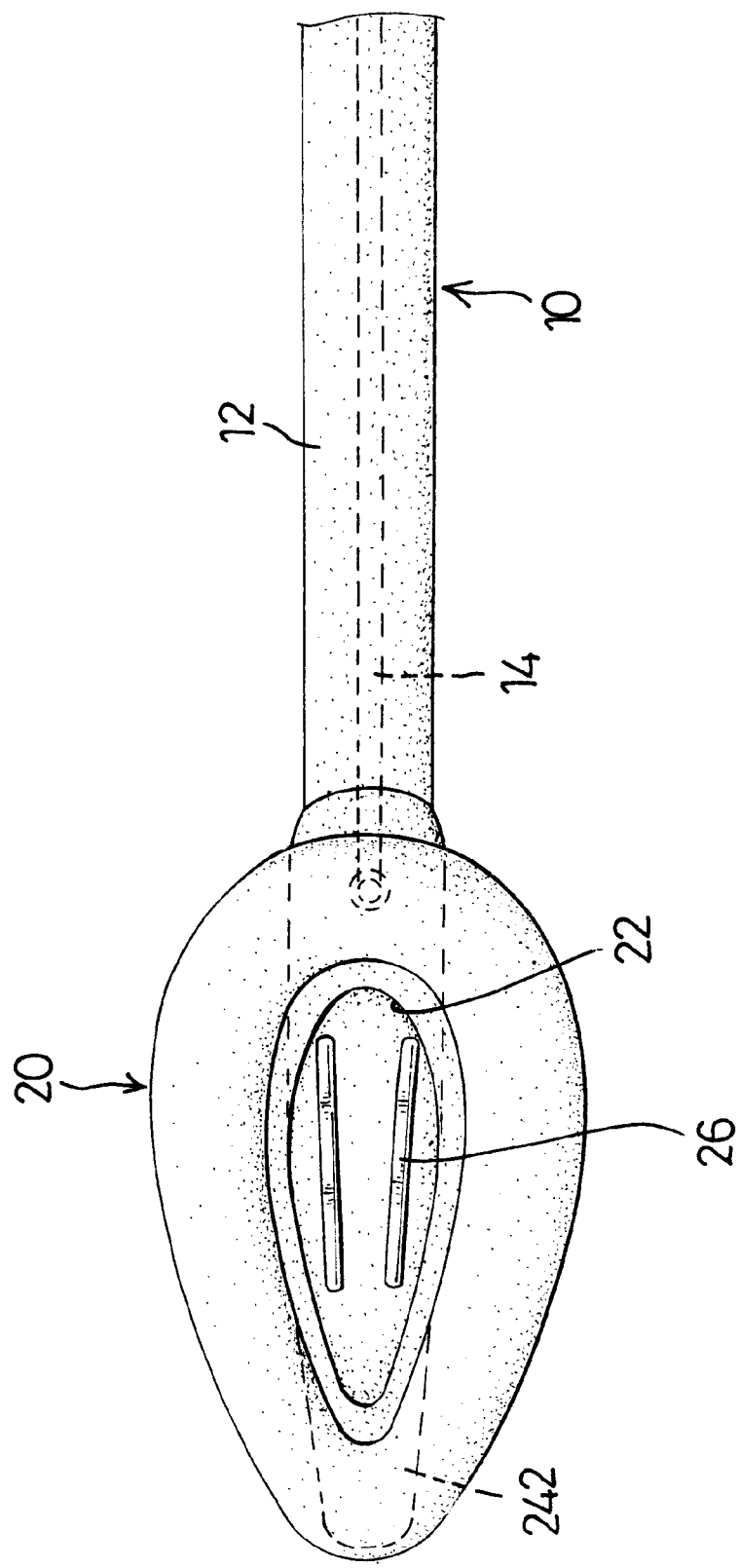
FIG. 3 is a top plan view of the laryngeal mask airway in FIG. 1.

With reference to FIGS. 1, 2 and 3, a laryngeal mask airway in accordance with the present invention comprises a dual-airway tube (10), a laryngeal mask (20) and a laryngeal mask inflation indicator device (30).

The dual-airway (10) has a connecting end and is composed of a primary tube (12) with an inner wall and a secondary tube (14) combined with the primary tube (12). The primary tube (12) is a large-bore tube made of resilient plastic material and communicates with the laryngeal mask (20) at the connecting end. The secondary tube (14) is formed inside walls of the primary tube (12) and emerges from the primary tube (12) a distance from laryngeal mask (20) to connect to the inflation indicator device (30).

The laryngeal mask (20) is teardrop-shaped to adapt to the larynx and is divided into a curved bottom face (not numbered) adjacent to the primary tube (12) and a bladder (24) around the curved bottom face. An opening (22) is defined in the curved bottom face to communicate with primary tube (12) and at least one rib (26) radially and longitudinally projects from the inner wall of the primary tube (12) near the opening (22). The bladder (24) having a pointed end and a rear obtuse end is made of soft material such as polyvinyl chloride (PVC) and has a tongue (242) extending forward from of the bottom face to protrude into the bladder (24) at the pointed end and having a free end away from the bladder (24). The secondary tube (14) is attached to, communicates with and inflates the bladder (24) by a syringe connected to the inflation device (30) via the secondary tube (14).

The inflation indicator device (30) connected to the secondary tube (14) is conventional. To avoid unnecessary repetition of known knowledge and techniques, no further description of the inflation indicator device (30) is provided.

Figure 4:
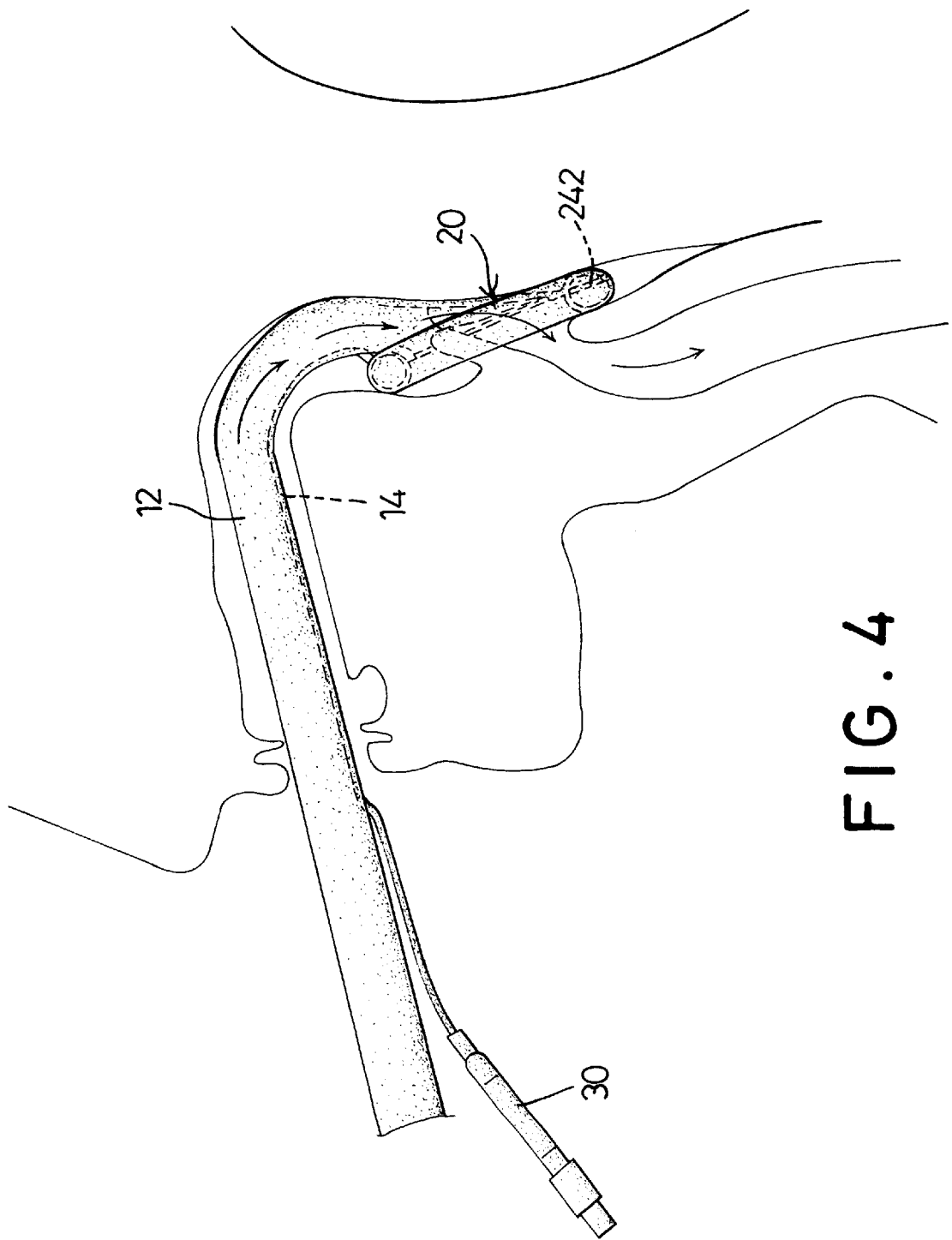
FIG. 4 is an operationally side plan view of the laryngeal mask airway inserted into the esophagus and over the larynx of a patient.
Figure 5:
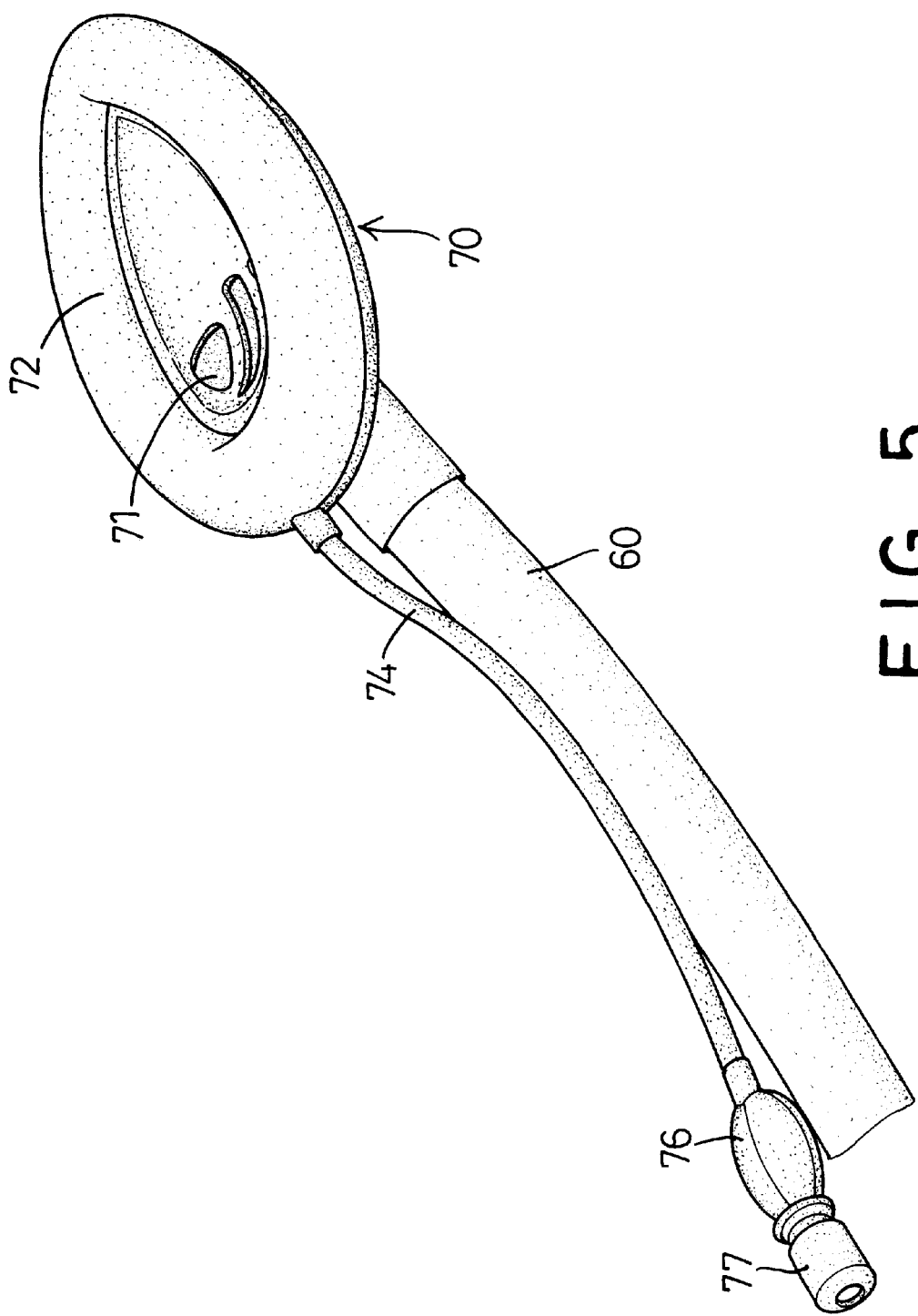
FIG. 5 is a perspective view of an conventional laryngeal mask.
Figure 6:
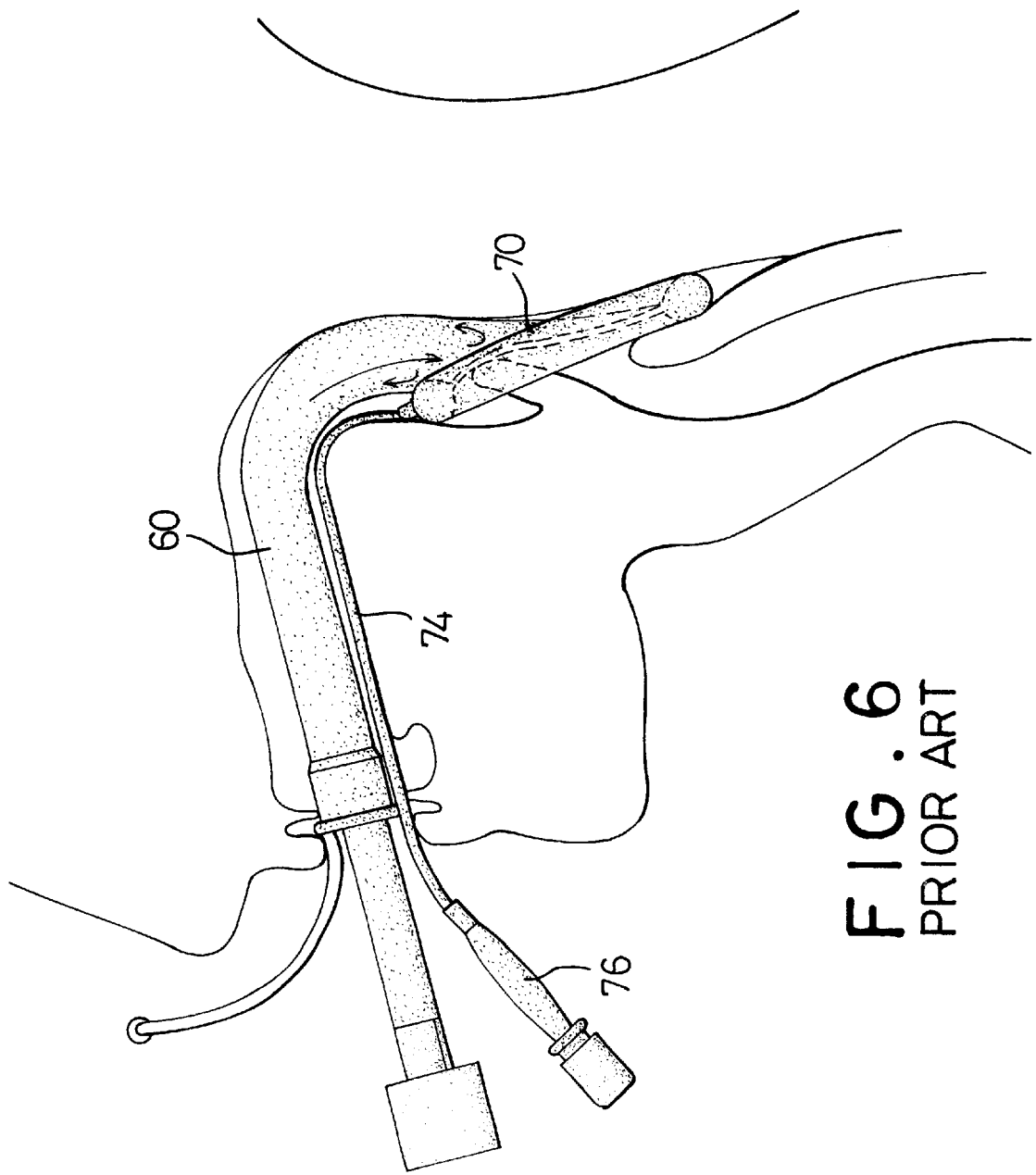
FIG. 6 is an operational side plan view of the conventional laryngeal mask airway inserted into the esophagus and over the larynx of a patient.

With reference to FIG. 4, the laryngeal mask airway has the following advantages:

1. The tongue (242) at the pointed portion inside the bladder (24) prevents the bladder (24) from refolding at the pointed portion when the laryngeal mask airway flattens inside the esophagus of the patient. Additionally, the bladder (24) made of PVC is soft to reduce the likelihood of larynx ulceration caused from undue pressing on the larynx.

2. The dual-airway tube (10) combines the primary tube (12) and the secondary tube (14) and simplifies these tubes (12, 14) into an integral tube. Therefore, medical personnel do not have a cumbersome inflation tube (74) of the conventional laryngeal mask airway to manipulate and insertion and operation of the laryngeal mask airway is much easier.

3. The at least one rib (26) longitudinally projecting from the inner wall of the primary tube (12) near the opening (22) keep the epiglottis from blocking the airway opening, the anesthetic gas is allowed to flow smoothly under the epiglottis, around the at least one rib (26) and into the body of the patient.

Although the invention has been explained in relation to its preferred embodiment, it is to be understood that many other possible modifications and variations can be made without departing from the spirit and scope of the invention as hereinafter claimed.

What is claimed is:

1. A laryngeal mask airway adapted to be positioned over the larynx of a patient, and comprising:

a dual-airway (10) composed of a primary tube (12) and a secondary tube (14) combined with the primary tube (12), the secondary tube (14) having a first end and a second end;

a mask (20) adapted to cover the larynx and divided into a curved bottom face adjacent to the primary tube (12) and an inflatable bladder (24) with a pointed end and a rear obtuse end around the curved bottom face that is connected to the first end of the secondary tube (14) near the rear obtuse end, the mask (20) having an opening (22) defined in the curved bottom face to communicate with the primary tube (12); and an inflation indicator device (30) connecting to the second end of the secondary tube (14);

wherein the improvements of the laryngeal mask airway comprise:

at least one rib (26) longitudinally formed inside the primary tube (12) near the opening (22) and adapted to prevent the epiglottis from covering the opening (22) so gases can be transmitted into and out of the patient; and a tongue (242) extending from the curved bottom face and entering inside the bladder (24) at the pointed end to prevent the bladder (24) from refolding wherein the tongue (242) erects inside the bladder (24) and has a free end away from the bladder (24).

2. The laryngeal mask airway as claimed in claim 1, wherein two ribs (26) are formed inside the primary tube (12).

3. The laryngeal mask airway as claimed in claim 2, wherein the secondary tube (14) is embedded inside walls of the primary tube (12).

4. The laryngeal mask airway as claimed in claim 2, wherein the inflation indicator device (30) is an inflation indicator balloon (76) with a valve (77).

5. The laryngeal mask airway as claimed in claim 1, wherein the secondary tube (14) is embedded inside walls of the primary tube (12).

6. The laryngeal mask airway as claimed in claim 5, wherein the inflation indicator device (30) is an inflation indicator balloon (76) with a valve (77).

7. The laryngeal mask airway as claimed in claim 1, wherein the inflation indicator device (30) is an inflation indicator balloon (76) with a valve (77).

8. The laryngeal mask airway as claimed in claim 1, wherein the bladder (24) is made of polyvinyl chloride (PVC).

* * * * *